United States Patent
Bi et al.

(10) Patent No.: US 10,830,850 B2
(45) Date of Patent: Nov. 10, 2020

(54) OPTICAL CAMERA FOR PATIENT POSITION MONITORING

(71) Applicant: Siemens Healthcare GmbH, Erlangen (DE)

(72) Inventors: Xiaoming Bi, Oak Park, CA (US); Uday Bhaskar Krishnamurthy, St. Louis, MO (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/371,186

(22) Filed: Apr. 1, 2019

(65) Prior Publication Data
US 2020/0309880 A1    Oct. 1, 2020

(51) Int. Cl.
| | |
|---|---|
| G01R 33/48 | (2006.01) |
| G01R 33/54 | (2006.01) |
| G01R 33/3415 | (2006.01) |
| G01R 33/30 | (2006.01) |
| G06T 7/00 | (2017.01) |

(52) U.S. Cl.
CPC ......... *G01R 33/481* (2013.01); *G01R 33/307* (2013.01); *G01R 33/3415* (2013.01); *G01R 33/543* (2013.01); *G06T 7/0012* (2013.01); *G06T 2207/10088* (2013.01); *G06T 2207/30196* (2013.01)

(58) Field of Classification Search
CPC .............. G01R 33/481; G01R 33/543; G01R 33/3415; G01R 33/307; G01R 33/4808; G06T 7/0012; G06T 2207/10088; G06T 2207/30196
See application file for complete search history.

(56) References Cited

U.S. PATENT DOCUMENTS

| | | |
|---|---|---|
| 9,753,111 B2 | 9/2017 | Forthmann et al. |
| 2002/0118280 A1 | 8/2002 | Medlar et al. |
| (Continued) | | |

FOREIGN PATENT DOCUMENTS

| | | |
|---|---|---|
| CN | 103445865 A | 12/2013 |
| DE | 10109219 B4 | 7/2005 |
| (Continued) | | |

OTHER PUBLICATIONS

Joint Commission. "National patient safety goals effective Jan. 1, 2015." Hospital Accreditation Program (2015).

(Continued)

*Primary Examiner* — Rishi R Patel

(57) ABSTRACT

A method includes capturing a first set of optical images of the subject while a subject is lying on a table of a Magnetic Resonance (MR) scanner. This first set of optical images is acquired without any MR phased-array coils placed on the subject. While the subject continues to lie on the table of the MR scanner, a second set of optical images of the subject is acquired with the MR phased-array coils placed on the subject. Aside from the optical images, a set of MR images of the subject is acquired using the MR scanner. The first and second set of optical images are registered to the MR images. Following registration, the first and second set of optical images are used to determine element positioning of the MR phased-array coils in the set of MR images.

18 Claims, 5 Drawing Sheets

(56) References Cited

U.S. PATENT DOCUMENTS

2013/0342851 A1* 12/2013 Dresel .................. A61B 5/0064
356/601
2016/0091583 A1    3/2016  Saybasili et al.
2016/0109212 A1    4/2016  Forthmann et al.
2016/0109545 A1    4/2016  Forthmann et al.
2016/0259019 A1*  9/2016  Gross ..................... A61B 5/055
2018/0014745 A1    1/2018  Senegas et al.

FOREIGN PATENT DOCUMENTS

JP      2018503455 A    2/2018
KR     20160076487 A    6/2016

OTHER PUBLICATIONS

Advisory, Pennsylvania Patient Safety. "Applying the universal protocol to improve patient safety in radiology." Pennsylvania Patient Safety Authority 8.2 (2011): 63-70.

* cited by examiner

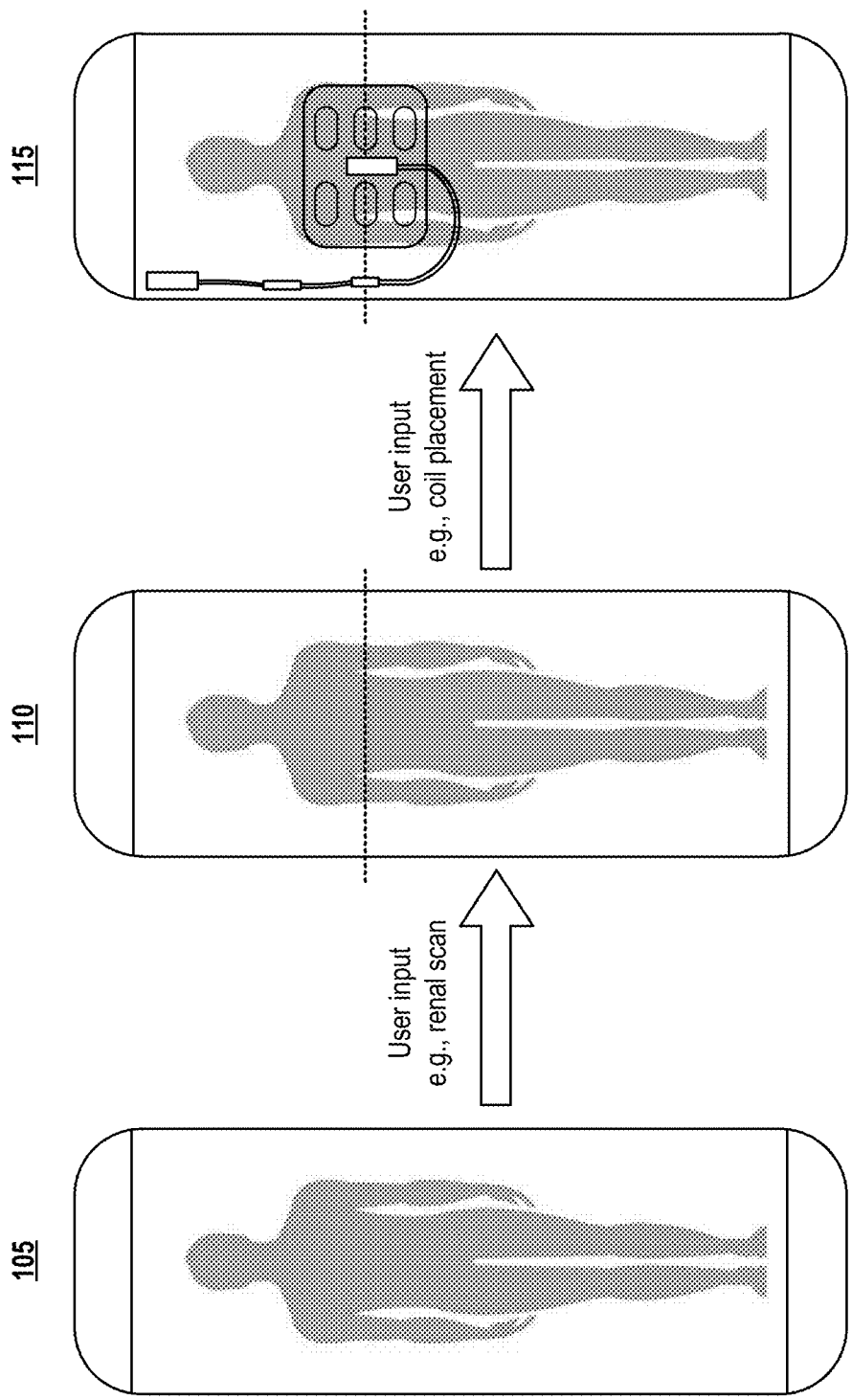

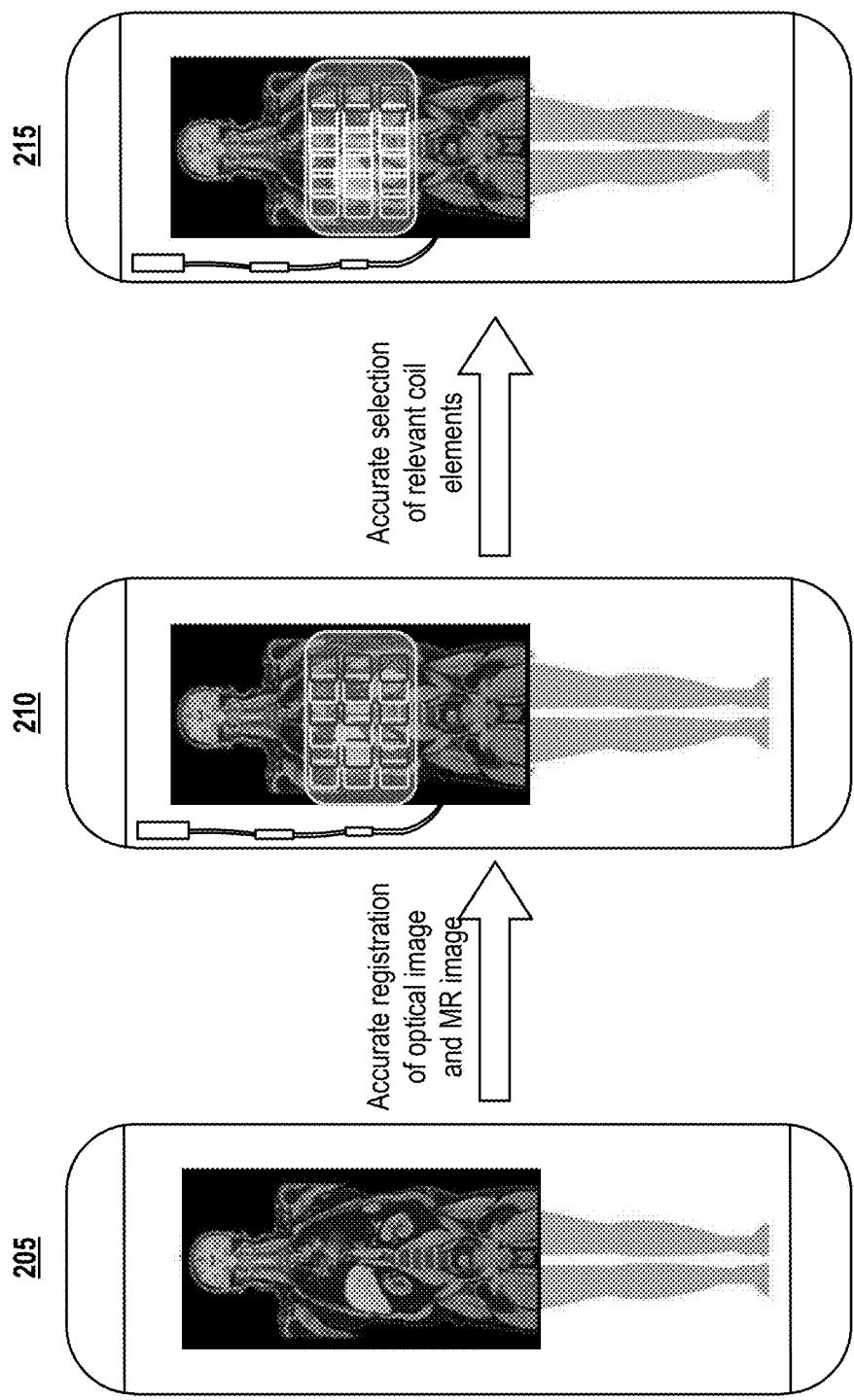

OPTICAL CAMERA FOR PATIENT POSITION MONITORING

TECHNICAL FIELD

The present invention relates generally to a patient positioning system and, more particularly, to an optical camera for patient position monitoring and for other image acquisition/reconstruction tasks. The techniques described herein are applicable to image scanners of various modalities including, without limitation Magnetic Resonance Imaging (MRI) scanners and combined MRI/positron emission tomography (PET) scanners.

BACKGROUND

Improving workflows for medical imaging procedures is critical to maximize the patient throughput and also to minimize errors from manual data entry and other operator-dependent operations. Despite technical developments and quality improvement efforts in medical imaging workflows, the prevalence of errors remains to be high. Many of these errors are related to mistakes made by technicians during manual input of imaging parameters. Technicians are typically multi-tasked to handle the entire process from patient handling, imaging system preparation and operation, communication with patients, radiologists, referring physician and other relevant personnel to post-processing of images. This complexity can introduce errors at various stages of the workflow.

Positioning tasks are the source of many mistakes that occur while performing imaging workflows. For example, during the registration stage, the technician is required to manually enter patient position parameters, while also interacting with the patient and, possibly, also performing other imaging preparation tasks. Furthermore, depending on the imaging modality and study being performed, the technician may be tasked with positioning of various apparatuses on the patient. One example of such apparatuses is the phased-array coils used during Magnetic Resonance Imaging (MRI).

MRI relies on local coils to collect signals from a targeted organ. Precise coil positioning is important to optimize the image quality by maximizing signal from targeted imaging object while minimizing signal contribution from other organs. Furthermore, having relevant coil elements and only those relevant coil elements activated can also contribute to optimal results. In practice, accurate relation between individual coil elements and anatomy is not always transparent to the user. Therefore the image SNR and quality could be compromised in case of suboptimal coil elements selection. In addition, for hybrid imaging systems such as PET-MR, accurate position of the coils is needed to account for attenuation due to the coils on the emission (PET) signal. While the attenuation characteristics of coils can be calculated using CT scans or other methods, the real-time localization of these coils has to be done independently for each scan to accurately compensate for PET signal attenuation caused by MR coils and other hardware.

Accordingly, patient positioning, relative positions of the coils and overall patient monitoring is increasingly necessary to mitigate errors from manual operations, help in automation of imaging processes, improve workflow and throughput, as well as create a more individualized approach for scanning protocols.

SUMMARY

Embodiments of the present invention address and overcome one or more of the above shortcomings and drawbacks, by providing methods, systems, and apparatuses related to using optical imaging for patient monitoring during MRI and other similar medical imaging procedures.

According to some embodiments, a method includes capturing a first set of optical images of the subject while a subject is lying on a table of a Magnetic Resonance (MR) scanner. This first set of optical images is acquired without any MR phased-array coils placed on the subject. While the subject continues to lie on the table of the MR scanner, a second set of optical images of the subject is acquired with the MR phased-array coils placed on the subject. Aside from the optical images, a set of MR images of the subject is acquired using the MR scanner. The first and second of optical images are registered to the MR images. Following registration, the first and second sets of optical images are used to determine element positioning of the MR phased-array coils in the set of MR images.

According to other embodiments, a system includes an MR scanner comprising a table, a plurality of MR phased-array coils, and an optical image camera. While a subject is lying on the table of the MR scanner, the optical captures a first set of optical images of the subject without the MR phased-array coils placed on the subject, as well as a second set of optical images of the subject with the MR phased-array coils placed on the subject. The MR scanner captures a set of MR images of the subject using the MR scanner, and registers the optical images to the MR images. Following registration, the MR scanner uses the first and second set of optical images to determine element positioning of the MR phased-array coils in the set of MR images.

According to another aspect of the present invention, a method includes capturing a set of optical images of the subject while a subject is lying on a table of a medical imaging scanner. The set of optical images are used to automatically determine positioning information describing body positioning of the subject on the table. Then, the positioning information may be registered with medical image scanner for use in acquiring additional images of the subject in one or more non-optical imaging modalities.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 1 shows a workflow that utilizes optical imaging, according to some embodiments of the present invention;

FIG. 2 shows an example of how such a system could be used to improve the image quality;

DETAILED DESCRIPTION

Figure 3A:
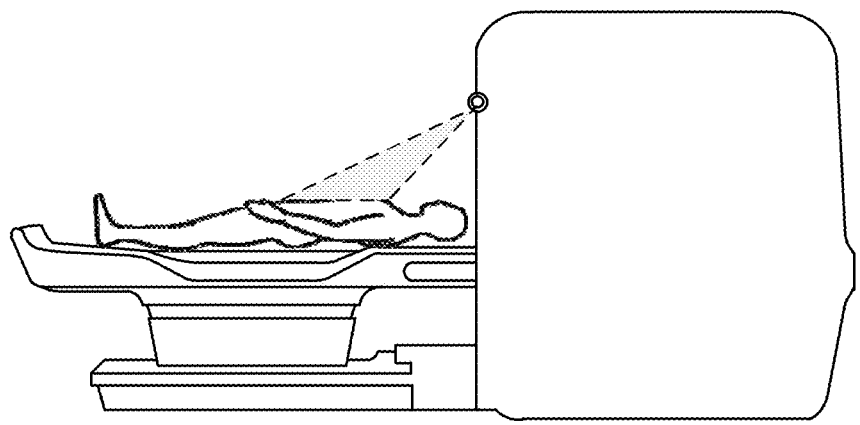
FIG. 3A shows an example of positioning an optical camera on a bore to acquire images of the subject as he or she is being positioned on the table.

Systems, methods, and apparatuses are described herein which relate generally to simplifying a Magnetic Resonance Imaging (MRI) workflow and optimizing image quality using an optical camera that captures snapshots of the patient as he or she is being positioned in the MRI scanner.

More specifically, the techniques described herein use an optical camera mounted on the gantry or in another area of the scanner room to capture images of the subject as he or she is being positioned prior to imaging. Subsequently, important information can be derived to simplify the workflow and optimize the image quality. The techniques described herein offer many benefits over conventional imaging systems. For example, the images acquired from the optical camera can be used to automatically define patient position (e.g., prone, spine, head first, feet first). The optical images may also be combined with a patient anatomy model to guide coil positioning and patient table (e.g., iso-center) positioning. The optical images may also be used in combination with physiological sensors to generate more individualized patient-specific SAR models. Furthermore, in the context of combined MRI/positron emission tomography (PET) scans, the optical images can be used to register the emission/PET scans to the coil position to accurately account for the signal attenuation due to the coils.

FIG. 1 shows a workflow that utilizes optical imaging, according to some embodiments of the present invention. The workflow is shown in 3 stages: 105-115. During stage 105, the subject lies on the table of the scanner and the optical imaging system (i.e., camera) begins to collect images and derives relevant information. The images may be still images or video images. The relevant information may include, for example, human pose information. For example, in FIG. 1, the subject is in a head-first, supine position. Once determined, the human pose information can be automatically fed into the patient registration system of the scanner without manual input from the operator as in conventional MR systems.

Techniques for human pose detection and generally known in the art and, in general, any technique executable by the computing system of the scanner (or a connected computing system) may be employed to determine the human pose information. For example, OpenPose is a human pose estimation library that uses neural networks and deep learning techniques to jointly detect a human body, head, hand, facial, and foot key points. OpenPose can operate in real-time. Thus, the key points can be collected as the patient is being positioned on the table. A machine learning model or rules-based system may then be applied to these key points to derive the human pose. For example, based on key points that may be derived from the image shown in FIG. 1, the human pose may be designated as "head-first supine." As an alternative to providing an explicit human pose, in some embodiments, the patient registration system may be configured to receive the key points directly from OpenPose (or a similar estimation system).

Furthermore, the subject's position with respect to the table can be determined by detecting the edges of the table (e.g., using markers on the table or through simple edge detection algorithms) and evaluating the location of key points with respect to those edges. For example, after the key point of the subject's head is known, the distance between that key point and the top edge can be used to determine how far up the subject is on the table. A similar measurement can be determined by calculating the distance between the foot key points and the bottom edge. Similarly, the distance between the left and right hand key points can be compared to the left and right edge of the table, respectively, to determine how far to the left or right on the table the subject is positioned.

Continuing with reference to FIG. 1, as soon as the exam is specified (e.g., a renal MRI scan) the optical images can be used to determine the position of an anatomical area of interest (e.g., kidney) based on a human model built into the scanner. For example, in embodiments where key points are determined, the key points can be used as model parameters to determine the geometric characteristics of the subject's anatomy. Once the geometry is known, the anatomical object uses this information and the human input to localize the anatomical area of interest. For example, based on key points for the shoulders, elbows, and pelvis, the location of the kidneys can be roughly approximated based on knowledge of kidney position within the human anatomy. Then, as shown in stages 110 and 115 of FIG. 1, a landmark can be generated to guide the optimal coil positioning. This helps to improve the consistency and accuracy of coil placement. In the example of FIG. 1, the landmark is a line projected by the scanner using laser light. However, it should be understood that other landmarks generally known in the art may be similarly employed.

Aside from use in the patient positioning task, the key points or other information describing the patient's position can be used for other imaging tasks. For example, current MRI systems measures the energy deposited to the imaging field in units of Watt/Kg, often referred to as SAR (specific absorption rate). This is calculated using standard human models and only corrected for height and weight for each individual patient. This restricts one from using all the features of MRI and often also misses local hotspots due to the non-individualized patient models. Additional parameters to the model like the length of torso, head circumference can be added to the model from optical images to further fine-tune the SAR calculation algorithms.

FIG. 2 shows an example of how such a system could be used to improve the image quality. As with FIG. 1, the example of FIG. 2 is shown in 3 stages 205-215. During the first stage, 3 sets of images are acquired: a first set of optical images of the subject without any MR phased-array coils placed on the subject, a second set of optical images of the subject with the MR phased-array coils placed on the subject, and one or more MR images. The MR images may be acquired, for example using a quick localization scan using a protocol such as FastView. As is generally understood in the art, FastView is proton-density weighted 2D axial acquisition technique where image data is acquired during continuous movement of the patient table. At stage 210, the optical images and MR images are co-registered. Because the surface coil is also visible in optical images along with images of the subject, such co-registration of optical images and MR images leads to accurate mapping of coil location with reference to MR images at stage 215.

Figure 3B:
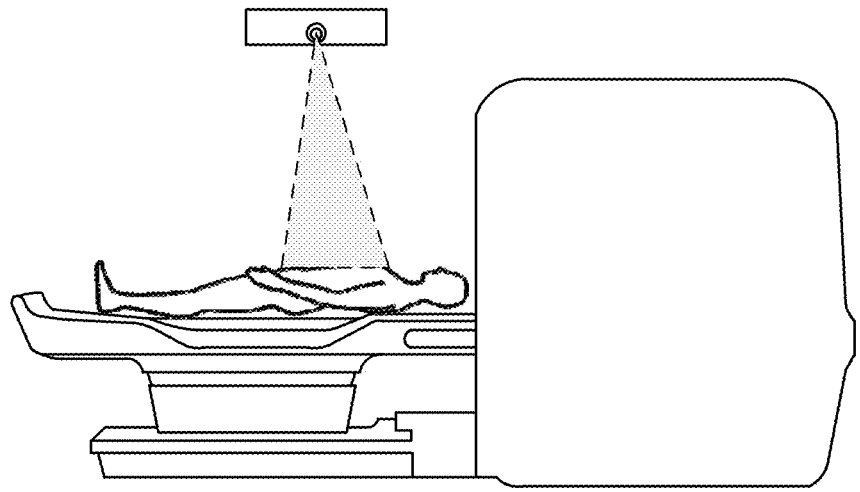
FIG. 3B shows an example of positioning an optical camera on the ceiling of a scanner room to acquire images of the subject as he or she is being positioned on the table.

FIGS. 3A and 3B show two examples of positioning of the optical camera to acquire images of the subject as he or she is being positioned on the table. In FIG. 3A, an optical camera is positioned at the top of the bore and angled to capture images of the subject. In FIG. 3B, the optical camera is mounted to a ceiling over the table to capture images immediately below it. It should be noted that these are not the only possibilities for camera placement. Additionally, multiple cameras may be used in some embodiments. For example, in one embodiment, the cameras shown in FIGS. 3A and 3B are used together. Alternatively (or additionally), cameras may be mounted in other positions of the scanner room (e.g., in the corners) to gather even more image data.

Figure 4:
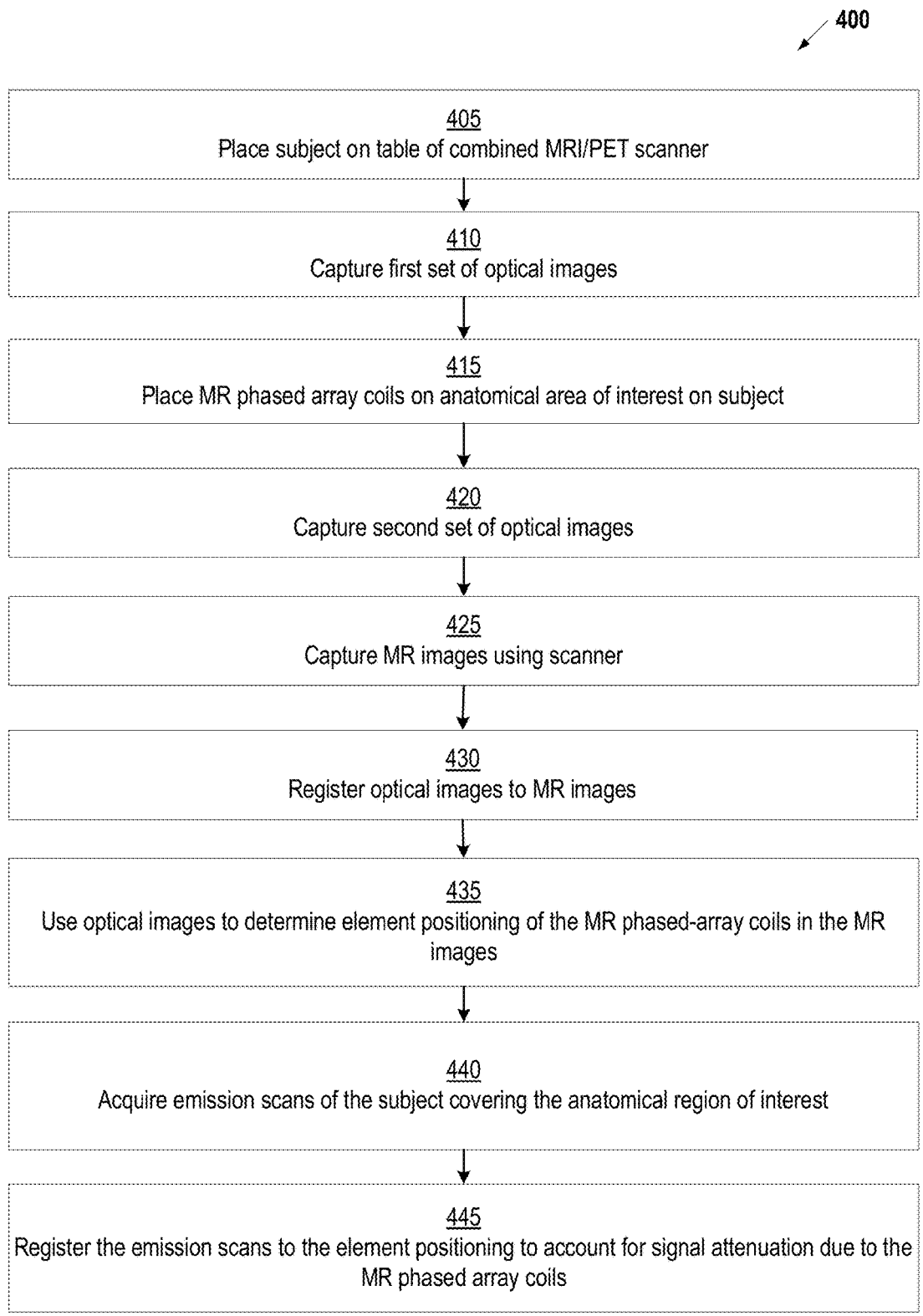
FIG. 4 shows a method for performing patient monitoring with an optical camera, according to some embodiments.

FIG. 4 shows a method 400 for performing patient monitoring with an optical camera, according to some embodiments. This example assumes that the scanner is a combined MRI/PET scanner. Starting at step 405, the subject is placed on the table of the scanner and positioned as necessary for the study being performed.

While a subject is lying on the table, a first set of optical images of the subject is captured at step 410. Next, at step 415, MR phase coils are positioned on the subject over an anatomical region of interest related to the study. In some embodiments, the scanner automatically detects the positioning of the subject on the table and the placement of the MR phase coils is based on this positioning. In one embodiment, a user inputs the type of exam that will be performed. The optical images captured in 410 are used in conjunction with an anatomical model to identify a location of the anatomical area of interest with respect to the table. Then, a landmark (e.g., laser light) is generated to guide placement of the MR phased-array coils placed on the subject location of the anatomical area of interest with respect to the table.

Continuing with reference to FIG. 4, at step 420 the scanner captures a second set of optical images of the subject with the MR phased-array coils placed on the subject. Then, at step 425, a set of MR images are acquired. The optical images are registered to the MR images at step 430 using one or more multi-modal image registration techniques known in the art. Once the image sets are registered, the optical images are used at step 435 to determine the element positioning of the MR phased-array coils in the set of MR images.

If the imaging device is a MRI machine, the method 400 may finish at step 435. However, if a combined MRI/PET scanner is employed, at step 440 emission scans of the subject covering the anatomical region of interest are acquired. These emission scans are registered to the element positioning at step 445 to account for signal attenuation due to the MR phased array coils. Aside from the emission scans, the element positioning may also be used to enhance MR imaging. For example, in one embodiment, the element positioning of the MR phased-array coils is used to select a subset of the MR phased-array coils most relevant to an anatomical region of interest associated with a study being performed using the MR scanner. Then, a new MR image of the subject covering the anatomical region of interest is acquired. During this acquisition, signals from the subset of MR phased-array coils are maximized during the acquisition while minimizing signal and noise from other MR phased-array coils, e.g., those coil elements far away from the targeted organ.

Figure 5:
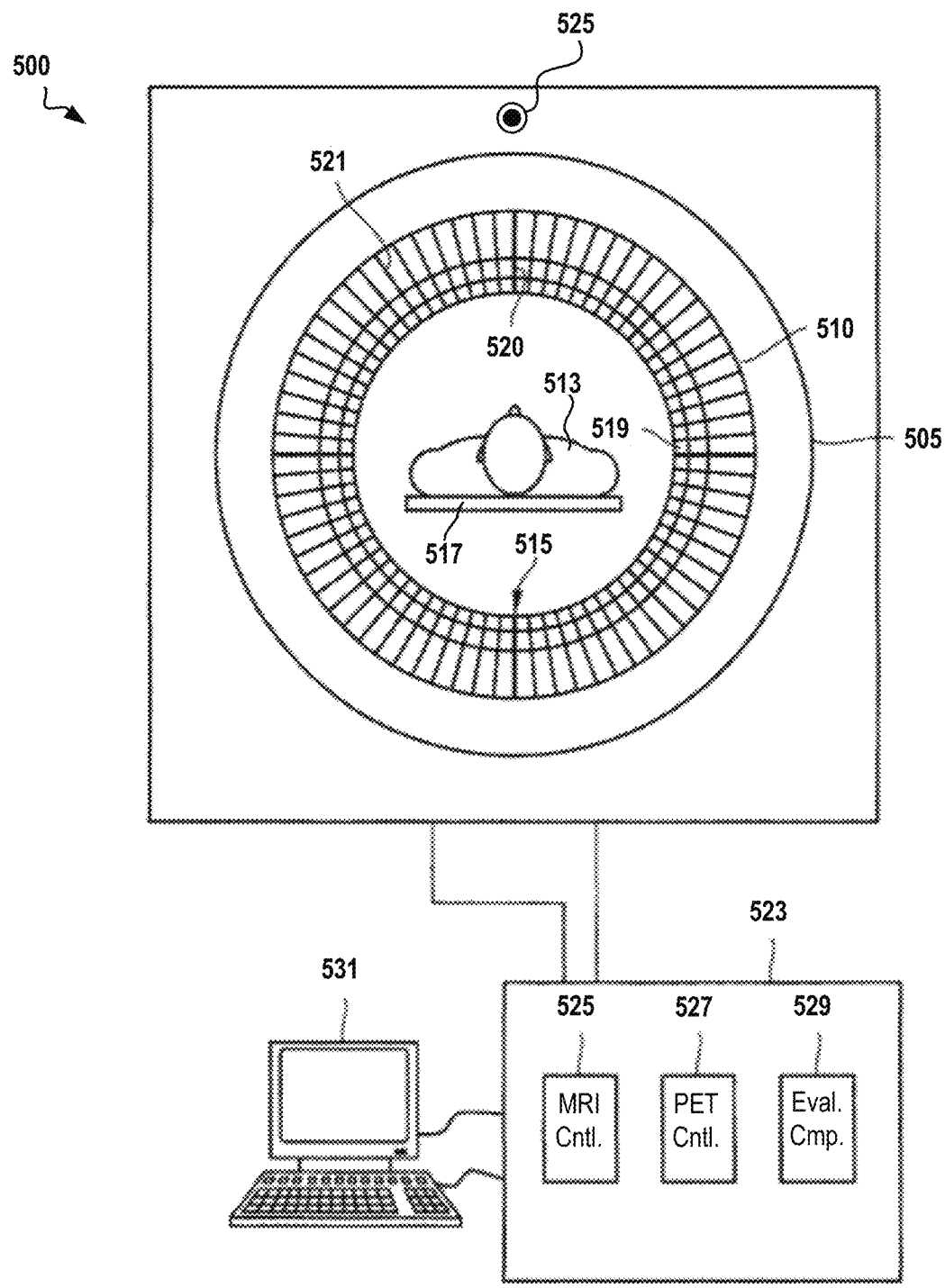
FIG. 5 is a schematic diagram of an exemplary MRI system, consistent with some of the disclosed embodiments.

FIG. 5 shows a known combined MRI/PET scanner 500 that is used in an example embodiment of the invention. An advantage of the combined MRI/PET scanner is that both MRI and PET data can be obtained isocentrically with targeted organ located at the isocenter position of both MR and PET detectors. Moreover, the measurement data can be recorded at the same time. In principle, parallel recording can also be undertaken if the MRI/PET scanner does not have an isocentric design. In this case, measurement data can be recorded simultaneously with both modalities, respectively for different regions.

The MRI/PET scanner 500 comprises a known tubular MRI Unit 505. The MRI unit 505 is only indicated schematically and defines a longitudinal direction z, which extends orthogonally to the plane of the drawing in FIG. 5. A PET Unit 510 is arranged coaxially within the MRI Unit 505. The PET Unit 510 comprises a plurality of PET Detection Units 515, arranged opposite one another in pairs about the longitudinal direction z. The PET detection units 515 preferably comprises an APD photodiode array 520 with an upstream array made of LSO Crystals 519 and an electric amplifier circuit 521. However, at least one embodiment of the invention is not restricted to the PET Detection Units 515 with the APD Photodiode Array 520 and the upstream array of LSO crystals 519; differently designed photodiodes, crystals, and devices can likewise be used for the purposes of detection. Finally, an Optical Camera 525 captures still images or records moving images of area within a field of view specified by the Optical Camera's 525 lens and other hardware components.

During an MRI and/or PET examination, the Subject 513 is successively moved to different positions by way of the Table 517 in order in each case to move the section to be examined into the examination region (field of view) of the MRI unit 505 and/or the PET unit 510. As described above, the Optical Camera 525 captures optical images of the Subject 513 while he or she is on the Table 517. This data may then be used, for example, to support positioning of the Subject 513 or related apparatuses (e.g., phased-array coils) during imaging.

The MRI/PET scanner 500 is controlled by a control device 523. The control device 523 in this example comprises a first component 525 for controlling the MRI unit 505 and a second component 527 for controlling the PET unit 510 for carrying out the PET measurement data recording. The components 525, 527 can likewise actuate the patient table 517 and position it correctly. Furthermore, the control device 523 further comprises an evaluation computer 529 that analyzes the recorded measurement data and is able to generate a hybrid image of the examination object that may then be presented on display computer 531. The control device 523 may also manage various tasks involved with integrating the images captured by the Optical Camera 525 into the imaging workflow (e.g., key point translation, image co-registration, etc.). In some embodiments, this functionality may be integrated into evaluation computer 529; in other embodiments, an additional component (not shown in FIG. 5) may be employed.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

The invention claimed is:

1. A method comprising:
while a subject is lying on a table of a Magnetic Resonance (MR) scanner, acquiring a first set of optical images of the subject without any MR phased-array coils placed on the subject;
while the subject is lying on the table of the MR scanner, acquiring a second set of optical images of the subject with the MR phased-array coils placed on the subject;
acquiring a set of MR images of the subject using the MR scanner;
registering the first and second set of optical images to the MR images;
following registration, using the first and second set of optical images to determine element positioning of the MR phased-array coils in the set of MR images.

2. The method of claim 1, further comprising:
detecting positioning of the subject on the table using the first set of optical images, wherein placement of the MR phased-array coils on the subject is based on the positioning.

3. The method of claim 2, further comprising:
receiving user input of a type of exam to be performed using the MR scanner, wherein the exam requires imaging of an anatomical area of interest;
using the first set of optical images and anatomical model to identify a location of the anatomical area of interest with respect to the table; and
generating a landmark to guide placement of the MR phased-array coils placed on the subject location of the anatomical area of interest with respect to the table.

4. The method of claim 3, wherein the landmark is a laser light projected across the anatomical area of interest.

5. The method of claim 1, further comprising:
using the element positioning of the MR phased-array coils to select a subset of the MR phased-array coils most relevant to an anatomical region of interest associated with a study being performed using the MR scanner;
acquiring a new MR image of the subject covering the anatomical region of interest, wherein signals from the subset of MR phased-array coils are maximized during the acquisition while minimizing signal and noise from other MR phased-array coils.

6. The method of claim 1, wherein the MR scanner is a combined MR/positron emission tomography (PET) scan and the method further comprises:
acquiring emission scans of the subject covering an anatomical region of interest; and
registering the emission scans to the element positioning to account for signal attenuation due to the MR phased array coils.

7. The method of claim 1, wherein the set of MR images are acquired using a quick localization scan.

8. The method of claim 7, wherein a quick localization scan is performed using a FastView localizer protocol.

9. A system comprising:
a Magnetic Resonance (MR) scanner comprising a table;
a plurality of MR phased-array coils;
an optical image camera configured to:
while a subject is lying on the table of the MR scanner, capture a first set of optical images of the subject without the MR phased-array coils placed on the subject;
while the subject is lying on the table of the MR scanner, capture a second set of optical images of the subject with the MR phased-array coils placed on the subject, wherein the MR scanner is configured to:
capture a set of MR images of the subject using the MR scanner;
register the first and second set of optical images to the MR images;
following registration, use the first and second set of optical images to determine element positioning of the MR phased-array coils in the set of MR images.

10. The system of claim 9, wherein the optical image camera is positioned on the MR scanner.

11. The system of claim 9, wherein the optical image camera is positioned on a ceiling above the MR scanner.

12. The system of claim 9, further comprising:
detecting positioning of the subject on the table using the first set of optical images, wherein placement of the MR phased-array coils is based on the positioning.

13. The system of claim 12, further comprising:
receiving user input of a type of exam to be performed using the MR scanner, wherein the exam requires imaging of an anatomical area of interest;

using the first set of optical images and anatomical model to identify a location of the anatomical area of interest with respect to the table; and generating a landmark to guide placement of the MR phased-array coils placed on the subject location of the anatomical area of interest with respect to the table.

14. The system of claim 13, wherein the landmark is a laser light projected across the anatomical area of interest.

15. The system of claim 9, further comprising:

using the element positioning of the MR phased-array coils to select a subset of the MR phased-array coils most relevant to an anatomical region of interest associated with a study being performed using the MR scanner;

acquiring a new MR image of the subject covering the anatomical region of interest, wherein signals from the subset of MR phased-array coils are maximized during the acquisition while minimizing signal and noise from other MR phased-array coils.

16. The system of claim 9, wherein the MR scanner is a combined MR/positron emission tomography (PET) scan and the system further comprises:

acquiring a new PET image of the subject covering an anatomical region of interest, wherein the element positioning is used to compensate for PET signal attenuation caused by the MR phased array coils.

17. The system of claim 9, wherein the set of MR images are acquired using a quick localization scan.

18. The system of claim 17, wherein quick localization scan is performed using a FastView localizer protocol.

* * * * *